United States Patent [19]

Hickmann

[11] 4,404,850
[45] Sep. 20, 1983

[54] ANEURYSM CLIP TESTING INSTRUMENT

[76] Inventor: Horst R. Hickmann, 1455 Montegor, Cincinnati, Ohio 45230

[21] Appl. No.: 338,367

[22] Filed: Jan. 11, 1982

[51] Int. Cl.³ .............................................. G01L 5/00
[52] U.S. Cl. ........................................ 73/161; 73/37; 73/862.53; 73/862.58
[58] Field of Search .............. 73/37, 168, 432 V, 161, 73/862.53, 862.58

[56] References Cited

U.S. PATENT DOCUMENTS 3,760,637 9/1973 Budinger .................................. 73/37
4,167,112 9/1979 Ressler .................................. 73/161
4,353,250 10/1982 Perlin ............................... 73/862.53

Primary Examiner—S. Clement Swisher
Attorney, Agent, or Firm—Frost & Jacobs

[57] ABSTRACT

An instrument used by surgeons to determine the suitability of an aneurysm or vascular clip just prior to its implantation. The primary component of the instrument is a test strip which comprises a first compartment, second compartment, and a tapered channel connecting these two compartments. The first compartment contains a colored fluid and means for forcing the fluid from the compartment into the tapered channel. The clip selected is attached to the test strip over the tapered channel. As the fluid is forced into the tapered channel and reaches the clip, the clip's effectiveness in impeding the pressurized fluid flow is observed. The pressure at which the clip fails is indicated on gauge means.

7 Claims, 4 Drawing Figures

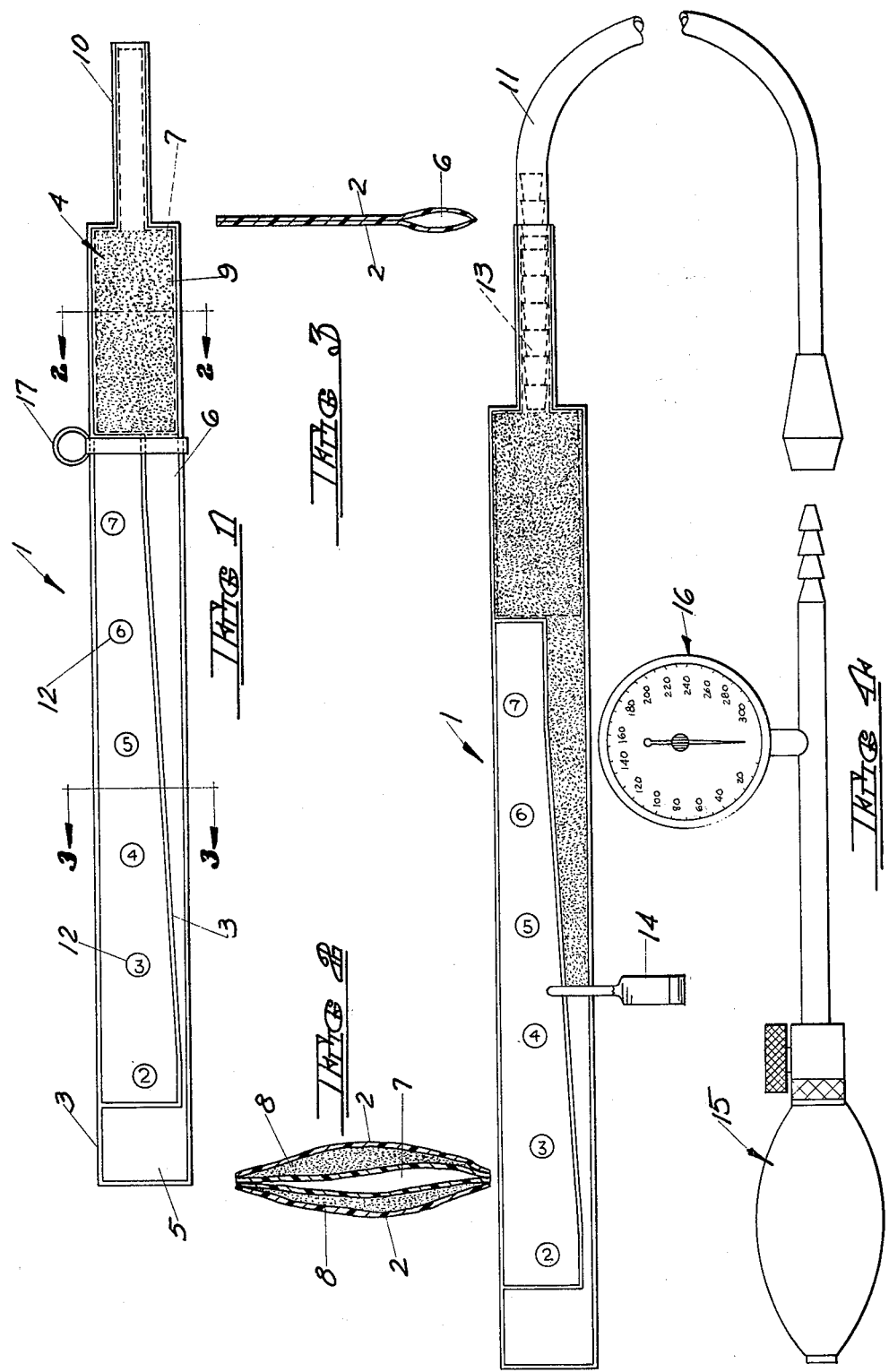

ANEURYSM CLIP TESTING INSTRUMENT

BACKGROUND OF THE INVENTION

The invention relates to an instrument used by a surgeon or other skilled worker in the operating room to test the suitability of a vascular or aneurysm clip prior to the implanting or application of such a clip.

DESCRIPTION OF THE PRIOR ART

An aneurysm is a sac formed by the dilatation of a blood vessel that results from disease of the vessel wall. To correct this abnormal condition on a blood vessel, surgeons have for many years used clips to isolate the aneurysm. However, radiology does not disclose sufficient details of a particular aneurysm to enable the surgeon to select a suitable clip in advance of the operative procedure. As is especially true in neurosurgery, the approach to the implant site makes the application of an aneurysm clip very difficult. For this reason, many clips are autoclaved for a particular operation, while only one will be selected for the implant. Thus, over a period of time any given clip prepared for use may have been autoclaved numerous times in the past and have been handled in a fashion damaging to its designed performance. Accordingly, after the surgeon has gone to great care in selecting the clip and taken considerable time and care in its application, the clip may fail necessitating the surgeon to repeat the time consuming process or possibly, causing even more disastrous results.

At present, no method or device has been available to the surgeon to enable him to verify the suitable performance or reliability of such clips during surgery and just prior to implantation.

SUMMARY OF THE INVENTION

The present invention is designed to enable a surgeon or other skilled worker to verify the suitability of an aneurysm clip in the operating room just prior to application of the clip. The invention simulates the pressure of the vascular system and the vessel or aneurysm neck diameter at the implant site of the patient. The various sizes or diameters are embodied in a component of the invention called a test strip. The clip selected for use in a given instance is attached to the test strip at a location which approximates the size of the vessel or aneurysm neck. The interior of the test strip is then fed with a colored fluid under pressure and the response of the clip at the relevant pressure is observed.

Thus, by using the present invention, the surgeon can tell immediately whether the clip will perform under conditions which simulate that of the patient. It is important to note that the entire test procedure is done on site just prior to the application of the clip. Such a procedure minimizes the possibility of failure of a clip and the resultant harm to the patient. In addition, should the clip fail for some unknown reason causing injury to the patient and the risk of threatened litigation against the doctor and hospital, the test procedure will establish verification that a suitable aneurysm clip was used.

BRIEF DESCRIPTION OF THE DRAWINGS

FIG. 1 is a front plan view of the test strip of the aneurysm clip testing instrument.

FIG. 2 is an enlarged cross-sectional view taken along the line 2—2 of FIG. 1.

FIG. 3 is an enlarged cross-sectional view taken along the line 3—3 of FIG. 1.

FIG. 4 is a fragmentary plan view illustrating the entire aneurysm clip testing instrument.

DETAILED DESCRIPTION

Shown in FIG. 1, indicated generally at 1, is the primary component of the aneurysm clip testing instrument, referred to as a test strip. The test strip 1 is an elongated, thin structure formed from overlying sheets 2 of a synthetic material that has physical properties similar to blood vessel tissue, as illustrated in FIG. 2. The overlying sheets 2 are bonded together by a heat sealing process in the preferred embodiment, but may be held together by any means that can be sterilized. The process of heat sealing the sheets 2 forms boundary lines 3 for the test strip 1 and its structural elements.

The elements of the test strip 1, as defined by the boundary lines 3, are a first compartment 4, a second compartment 5, and a tapered channel 6 which connects the first compartment 4 and second compartment 5. Although the test strip 1 is described as having the first compartment 4, tapered channel 6, and second compartment 5, it will, of course, be understood that these elements are not physically separate but connect internally to define a single volume.

In the preferred embodiment, the first compartment 4 contains an inflatable air bag 7 and a colored fluid 8 indicated by the shading. The cross-sectional view of FIG. 2 shows the orientation of the air bag 7 and the colored fluid 8. As will be more fully described hereinafter, the inflatable bag 7 serves as means for forcing the colored fluid 8 from the first compartment 4 under pressure. Again, it will be understood that other structures, such as a cylinder-piston arrangement, could also serve this function. To provide realistic test conditions, the colored fluid 8 is preferably red and has flow properties comparable to human blood. The only function of the second compartment 5 is to receive the spent colored fluid 8 after the test. In the preferred embodiment, the first compartment 4 has an enlarged portion 9 and a narrow neck portion 10, the narrow neck portion 10 being sized to facilitate easy connection of the test strip 1 to an air hose 11, as shown in FIG. 4.

The tapered channel 6, shown in cross-section in FIG. 3, is greatest in width where it adjoins the first compartment 4 and gradually narrows to its smallest width where it adjoins the second compartment 5. Adjacent the tapered channel 6 is numbered indicia 12 which communicate to the user the vessel diameter corresponding to the width of the channel 6 at the respective locations. Preferably, the indicia 12 are formed in the test strip 1 by the heat seal process; alternatively, the indicia could be scribed or etched into the surface of the test strip 1 separate from the heat seal process.

Prior to use, the test strip 1 is sterilized, vacuumized, filled with the appropriate amount of the colored fluid 8 and fitted with a shipping clip 17 to confine the fluid 8 within the first compartment 4. An adapter fitting 13 is connected to the inflatable air bag 7 within the first compartment 4. An air hose 11 of the desired length is connected to the adapter fitting 13. These components, the test strip 1 (with fluid 8), the shipping clip 17, the adapter fitting 13, and the air hose 11, comprise a presterlized package and would be part of the overall instrument package which is opened prior to surgery on the instrument table.

During the course of an operation, the surgeon determines the size of the blood vessel or aneurysm neck to which a clip is to be applied. The surgeon will select a corresponding diameter on the tapered channel 6 of the test strip 1, apply the clip 14 that has been selected for the implant and remove the shipping clip 17. To complete the testing instrument of the present invention, the air hose 11 is connected to a source of pressurized air 15 having gauge means 16. Upon the request of the surgeon, the source of pressurized air 15 is used to inflate the air bag 7. As the air bag 7 expands, the colored fluid is forced from the first compartment 4 into the tapered channel 6 until it reaches the point where the clip 14 has been applied. As soon as the surgeon detects leakage of the colored fluid 8 beyond the clip 14, the pressure reading on the gauge means 16, such as a sphygmomanometer, is noted. If the pressure reading is lower than the patient's systolic blood pressure, the clip 14 is considered unsuitable for application. A pressure reading which is higher than the patient's systolic blood pressure, plus an additional safety margin, will assure the reliability of that clip 14 for its intended purpose. For record keeping purposes the clip 14, vessel diameter tested and the pressure reading on the gauge means 16 would then be recorded in the surgical notes for future reference.

After the test is completed, the clip 14 is removed from the test strip 1 and the spent colored fluid 8 flows on into the second compartment 5. If the clip 14 proves to be suitable, it is implanted by the surgeon. If the test shows that the clip 14 would not perform satisfactorily, the clip 14 is discarded and the test procedure is repeated with another clip.

In an alternative embodiment of the aneurysm clip testing instrument, the first compartment 4 of the test strip 1 would contain neither the air bag 7 nor the colored fluid 8; accordingly, the shipping clip 17 would not be necessary. Having this structure, the instrument would test the clip 14 with air pressure alone, producing more critical results. The test procedure would be similar to that outlined previously, except that the surgeon would not detect leakage past the clip 14. Instead, the gauge means 16 would indicate the pressure when air leakage occurs without inflating the second compartment 5 excessively.

As should now be apparent, the invention provides a unique aneurysm clip testing instrument especially suited for on-site testing of clips to be used in surgery. However, it will, of course, be understood that variations and modifications can be made without departing from the spirit and purpose of the invention.

What is claimed is:

1. An instrument for testing vascular and aneurysm clips by simulating the pressure of the vascular system and the diameter of the vessel at the implant site, said instrument comprising:

an elongated, thin test strip having a first compartment, a second compartment and a tapered channel connecting said first and second compartments;

means for filling said test strip with a fluid; and gauge means for indicating the pressure within said test strip;

whereby when one of said clips is applied across said tapered channel at a location corresponding in size to a vessel or aneurysm neck, and said test strip is filled with said fluid until the fluid reaches the location of said clip, with the pressure of said fluid being continually increased until said clip fails, the amount of pressure is indicated on said gauge means.

2. An instrument for testing vascular and aneurysm clips by simulating the pressure of the vascular system and the diameter of the vessel at the implant site, said instrument comprising:

an elongated, thin test strip having a first compartment, a second compartment and a tapered channel connecting said first and second compartments;

a colored fluid within said first compartment of said test strip;

means for forcing said fluid out of said first compartment and into said tapered channel; and gauge means for indicating the pressure within said test strip;

whereby when one of said clips is applied across said tapered channel at a location corresponding in size to a vessel or aneurysm neck, and said fluid is forced under pressure from said first compartment into said tapered channel until it reaches the location of said clip, with the pressure of said fluid being continually increased until said flip fails, the amount of pressure is indicated on said gauge means.

3. The testing instrument recited in claim 2 wherein said means for forcing said fluid is an inflatable air bag within said first compartment of said test strip.

4. The testing instrument recited in claim 3 wherein said test strip is formed from overlying sheets of flexible material bonded together.

5. The testing instrument recited in claims 2, 3 or 4 wherein said test strip is provided with indicia of the width of said tapered channel.

6. The testing intrument recited in claims 3 or 4 wherein said first compartment of said test strip has a narrowed neck portion adapted to receive a hose fitting.

7. The testing instrument recited in claims 2, 3 or 4 wherein said colored fluid has properties similar to that of human blood.

* * * * *